(12) United States Patent
Wang

(10) Patent No.: US 7,975,873 B2
(45) Date of Patent: Jul. 12, 2011

(54) BRACKET TYPE BIOGAS GAS-STORAGE COVER

(76) Inventor: Jian an Wang, Guangdong (CN)

( * ) Notice: Subject to any disclaimer, the term of this patent is extended or adjusted under 35 U.S.C. 154(b) by 544 days.

(21) Appl. No.: 11/992,453

(22) PCT Filed: May 15, 2006

(86) PCT No.: PCT/CN2005/000975
§ 371 (c)(1),
(2), (4) Date: Mar. 20, 2008

(87) PCT Pub. No.: WO2007/033540
PCT Pub. Date: Mar. 29, 2007

(65) Prior Publication Data
US 2010/0140272 A1 Jun. 10, 2010

(30) Foreign Application Priority Data
Sep. 20, 2005 (CN) .......................... 2005 1 0037446

(51) Int. Cl.
*B65D 25/10* (2006.01)

(52) U.S. Cl. ........ 220/756; 220/752; 220/762; 220/754; 220/765

(58) Field of Classification Search .............. 220/367.1, 220/345.1, 752, 756, 762, 754, 765; 292/65, 292/111, 257, 105
See application file for complete search history.

(56) References Cited

U.S. PATENT DOCUMENTS

| 3,406,859 A | * | 10/1968 | Nachshen | 52/83 |
| 4,157,146 A | * | 6/1979 | Svenson | 220/324 |
| 6,595,716 B1 | * | 7/2003 | VanDeVyvere et al. | 404/26 |
| 6,880,589 B2 | * | 4/2005 | Camoli | 141/98 |

* cited by examiner

*Primary Examiner* — Anthony Stashick
*Assistant Examiner* — Kareen Rush
(74) *Attorney, Agent, or Firm* — Raymond Y. Chan; David and Raymond Patent Firm

(57) ABSTRACT

A bracket type biogas storage cover includes a cover with an exhaust vent, characterized in that there are at least two brackets which are used to fix the cover to a biogas digester's opening on the lower edge of the cover.

10 Claims, 3 Drawing Sheets

BRACKET TYPE BIOGAS GAS-STORAGE COVER

BACKGROUND OF THE PRESENT INVENTION

1. Field of Invention

The present invention relates to a movable gas storage cover of a hydraulic biogas fermentation device, and particularly to a bracket type biogas gas storage cover.

2. Description of Related Arts

The China patent number ZL03201184.3 "Foldable Biogas Digester Cover" disclosed a removable gas storage cover for biogas digester, wherein three reinforcing beams are provided on top of the removable cover. Removable connectors are mounted on the reinforcing beams. The removable connectors can be plugged into the inner edge of the opening of the biogas digester so that the removable cover can be fixed inside the opening of the biogas digester. Because the removable cover is fixed via the removable connectors, the removable cannot be upwardly floated at the time when the biogas is stored in the removable cover. Practically, such structural configuration is useful in practice but still have some disadvantages. The removable cover is fastened to the opening of the gas storage by the three reinforcing beams to prevent the removable cover from floating upward. In other words, the three reinforcing beams exert the downward force to push down the removable cover from the top thereof. However, when the removable cover is exerted by the gas pressure inside the biogas digester, the removable cover is deformed especially with the resistance from the reinforcing beams. Therefore, the removable cover must be configured to have high stiffness and strength for anti-deformation. This will increase the production cost and limit the service life span of the removable cover.

SUMMARY OF THE PRESENT INVENTION

According to the disadvantage of the conventional hydraulic biogas digesters, the main object of the present invention is to provide a bracket gas storage cover which can largely reduce the requirement of the stiffness and strength for preventing the deformation, reduce the fabrication cost, and increase the service life span.

Accordingly, in order to accomplish the above objects, the present invention provides a bracket type biogas gas-storage cover, comprising a cover having an air vent, a reinforcing ring provided at an opening edge, and at least two brackets spacedly provided the reinforcing ring for affixing the opening edge of the cover at the opening of the biogas digester.

Preferably, there are three brackets evenly provided at the opening edge of the cover.

The principle of present invention is that the cover is mounted to the biogas digester by coupling the lower opening edge of the cover with the opening of the biogas digester. Unlike the conventional structure of the cover by coupling the top of the cover with the biogas digester, the stress points of the cover shift to the lower opening edge thereof. In other words, the pressure will not be exerted at the top of the cover. Therefore, the cover can retain its hemispherical shape for preventing the cover from being deformed by the pressure. Accordingly, the cover requires having a predetermined stiffness and strength at the opening edge to couple with the opening of the biogas digester. Therefore, there is no particular physical configuration of the cover to maintain a predetermined stiffness thereof. In addition, the strength of the cover can be relatively low. In other words, the cover can even be made of soft material.

Accordingly, the force distribution of the cover is more efficient. The stiffness and strength requirement of the cover can be substantially lowered. The production cost of the cover can be significantly reduced. In addition, the life span of the cover can be greatly extended.

The bracket biogas gas-storage cover of the present invention is efficient, convenient and practical. It is easy to mount the cover within the opening of the biogas digester by using the plugs and the brackets. The present invention not only provides all the functions of the conventional gas cover to satisfy the requirements of the normal use, but also overcomes the drawbacks of the conventional gas cover including the strict requirements of the material, high production cost and short life span.

These and other objectives, features, and advantages of the present invention will become apparent from the following detailed description, the accompanying drawings, and the appended claims.

DETAILED DESCRIPTION OF THE PREFERRED EMBODIMENT

Figure 1:
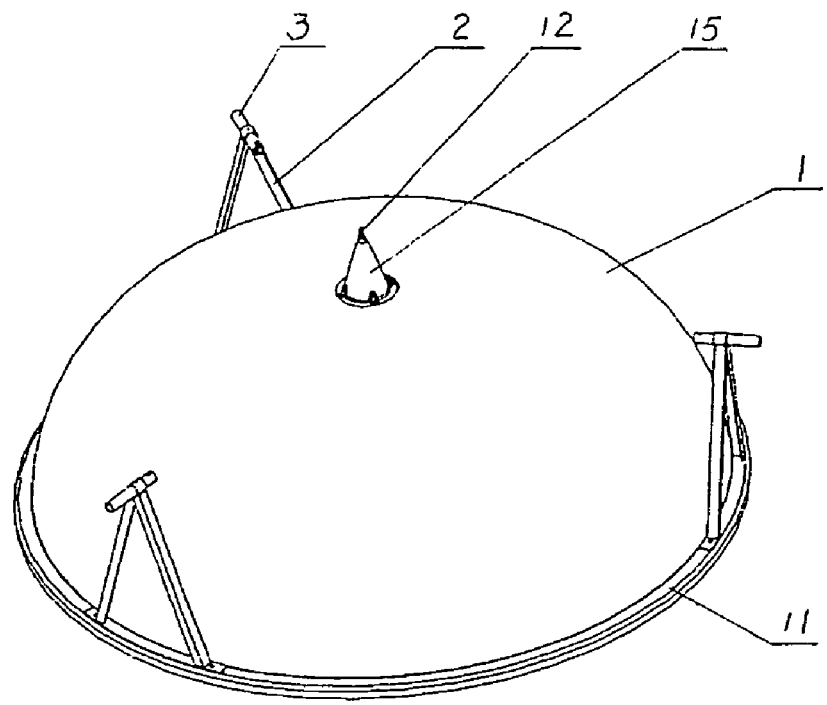
FIG. 1 is the perspective view of a bracket type biogas storage cover according to a preferred embodiment of the present invention.
Figure 2:
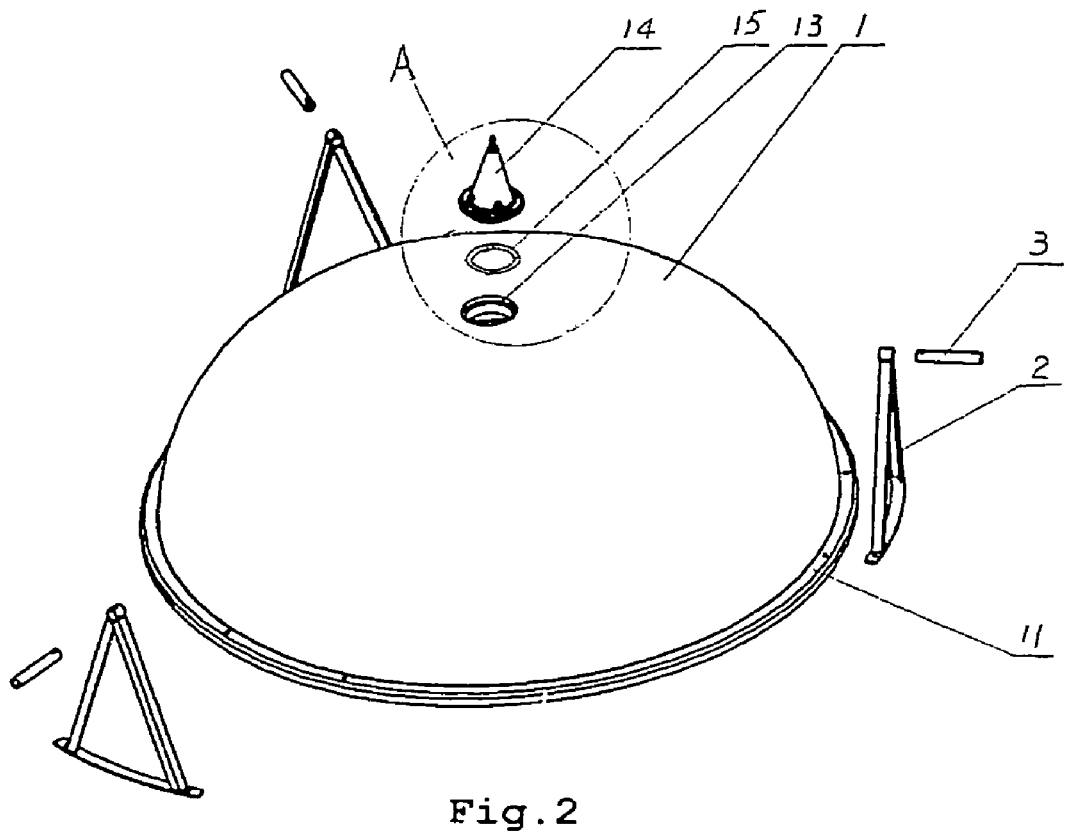
FIG. 2 is an exploded schematic view of the bracket type biogas storage cover according to the above preferred embodiment of the present invention.

Referring to FIGS. 1 and 2 of the drawings, a bracket type biogas storage cover for a biogas digester according to a preferred embodiment is illustrate, wherein the biogas storage cover, which is a biogas digester cover, comprises a cover 1 having an air vent 12 and a plurality of brackets 2. The cover 1 has a hemisphere shape. A reinforcing ring 11 is provided at an opening edge of the cover, wherein the air vent 12 is provided on top of the cover 1. Accordingly, there are three brackets 2 spacedly provided at the reinforcing ring 11 for coupling the opening edge of the cover 1 with the opening of the biogas digester.

Figure 3:
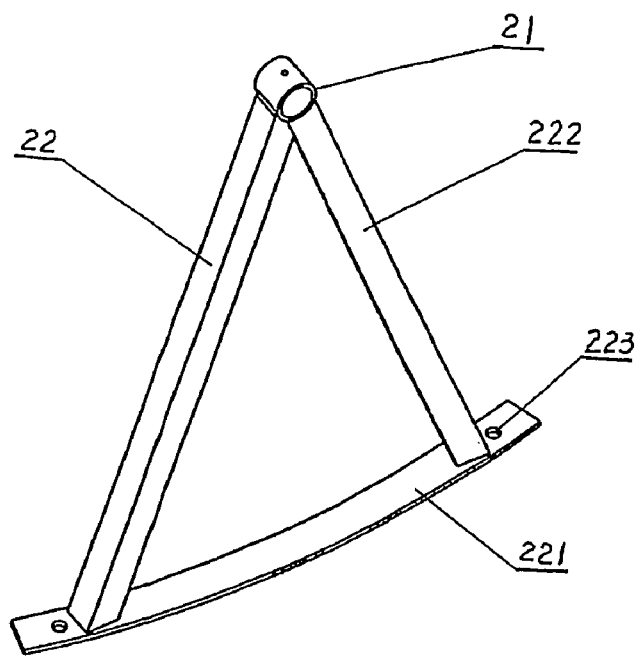
FIG. 3 is the schematic diagram of the bracket of the bracket type biogas storage cover according to the above preferred embodiment of the present invention.

As shown in FIG. 3, each of the brackets 2 comprises a supporting frame 22 having a triangular shape, and a locking sleeve 21 provided at the vertex of the supporting frame 22 for a pin locker 3 passing through the locking sleeve 21. The supporting frame 22 has a curved base 221 wherein a curvature of the curved base 221 matches with a curvature of the reinforcing ring 11. The supporting frame 22 further has a plurality of mounting holes 223 spacedly formed at the curved base 221 for the curved base 221 of the supporting frame 22 mounting at the reinforcing ring 11 via bolts and nuts.

Figure 4:
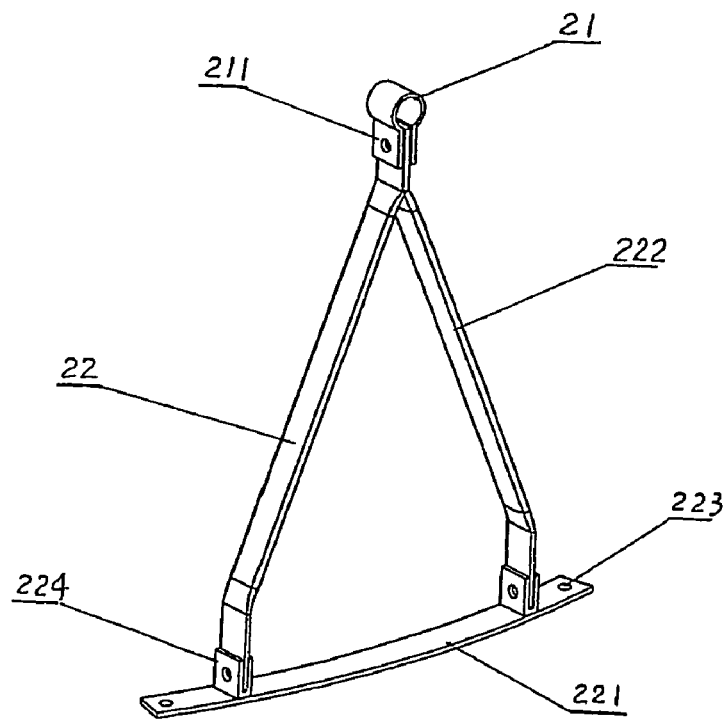
FIG. 4 illustrates an alternative mode of the bracket of the bracket type biogas storage cover according to the above preferred embodiment of the present invention.

FIG. 4 illustrates an alternative mode of the bracket 2, wherein the locking sleeve 21 is connected to the vertex of the supporting frame 22 via a hinge. Two hypotenuse edge frames 222 of the supporting frame 22 are also connected to the curved base 221 via two hinges respectively. Through the hinges, the locking sleeve 21 is pivotally coupled with the supporting frame 22 while the hypotenuse edge frames 222 are pivotally coupled with the curved base 221. Accordingly, such pivotal configuration of the supporting frame 22 facilitates the installation of the cover 1 to the biogas digester.

Accordingly, the locking sleeve 21 has a Ω-shaped horseshoe structure and has two fringes 211 extended from an opening of the locking sleeve 21, wherein a screw hole is provided at each of the fringes 211 for pivotally connecting to the supporting frame 22 via the corresponding hinge. Each of the hypotenuse edge frames 222 has a S-shaped structure. A screw hole is provided at each end of the hypotenuse edge frame 222. The supporting frame 22 further has two U-shaped connectors 224 spacedly provided at the curved base 221, wherein each of the U-shaped connectors 224 also has a screw hole formed thereon. Each of the hypotenuse edge frames 222 is pivotally coupled between the locking sleeve 21 and the curved base 221 by coupling the two ends of the hypotenuse edge frame 222 with the fringe 211 and the respective U-shaped connector to align the screw holes with each other, such that the screws are used as a connecting element to pivotally connect the hypotenuse edge frame 222 between the locking sleeve 21 and the curved base 221. Accordingly, the advantage of the pivotal configuration of the bracket is that the angle of the locking sleeve 21 with respect to the supporting frame 22 can be selectively adjusted. In addition, the angle of the hypotenuse edge frame 222 with respect to the curved base 221 can also be selectively adjusted. Therefore, the bracket type biogas gas-storage cover of the present invention can be easily mounted at the opening of the biogas digester.

Figure 5:
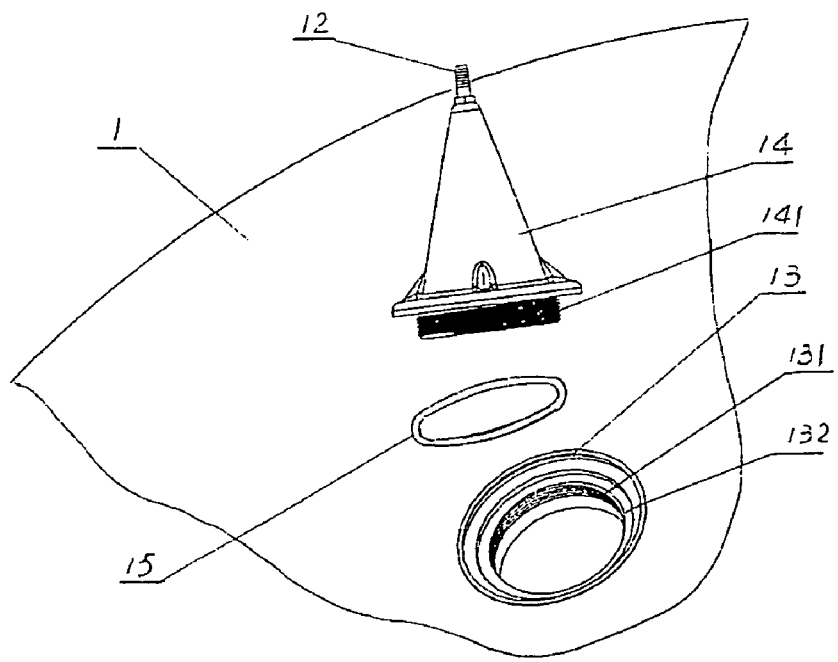
FIG. 5 is a partially enlarged schematic view of the bracket type biogas storage cover according to the above preferred embodiment of the present invention.

In order to release the pressure inside the biogas digester, the cover 1 further has a vent hole 13 formed at a top side thereof and comprises a sealing cap 14 sealed and mounted at the vent hole 13, as shown in FIG. 5. The vent hole 13 has an inner threaded portion 131 formed at an inner edge wall thereof and a shoulder edge portion 132 to support a sealing ring 15 thereat. The sealing cap 14 comprises an outer threaded portion 141 formed at a bottom edge to engage with the inner threaded portion 131 of the vent hole 13, wherein the sealing ring 15 is sealed between the bottom edge of the sealing cap 14 and the shoulder edge portion 132 of the vent hole 13. The air vent 12 is provided at the top end of the sealing cap 14.

Figure 6:
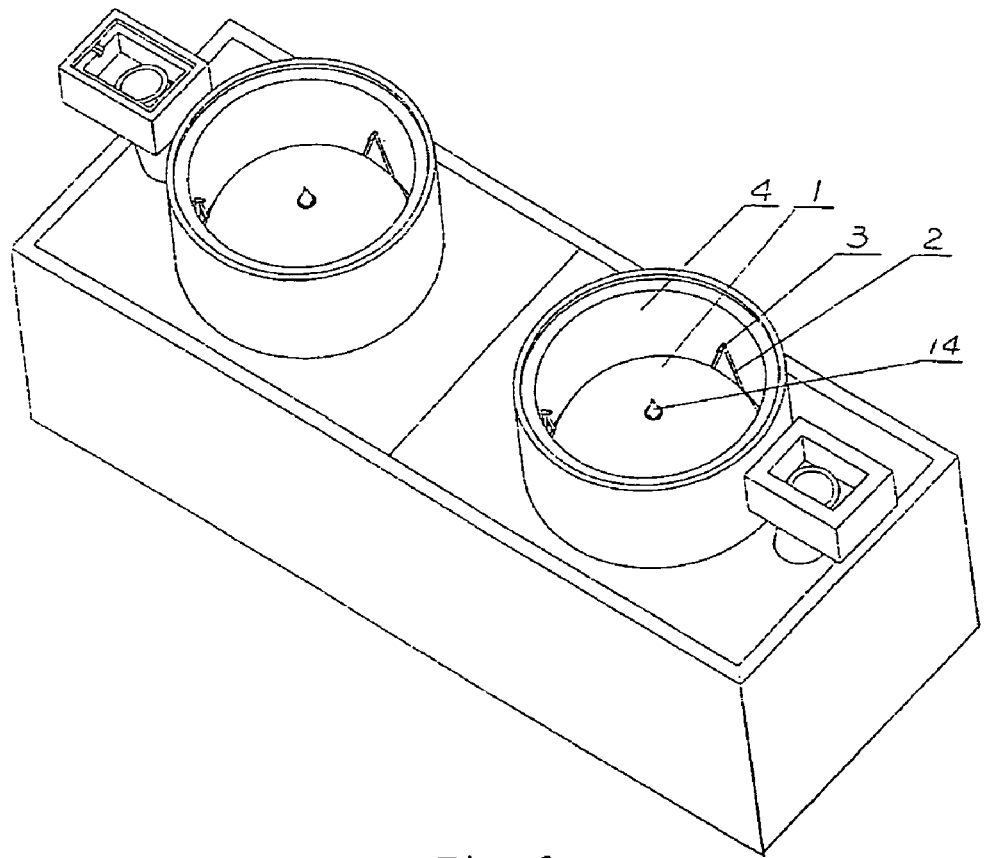
FIG. 6 is the schematic diagram of the bracket type biogas storage cover installed in a biogas digester according to the above preferred embodiment of the present invention.

As shown in FIG. 6, the bracket type biogas storage cover of the present invention is mounted at the opening of the biogas digester. Accordingly, a plurality of retention holes are spacedly formed, preferably by drilling, at an inner wall of the opening 4 of the concrete biogas digester with respect to the location of the locking sleeves 21 of the biogas storage cover. Then, when the cover 1 is coupled within the opening of the biogas digester to align the locking sleeves 21 with the retention holes respectively, pin lockers 3 are slidably extended through the locking sleeves 21 to engage with the retention holes respectively, so as to retain the cover 1 within the inner wall of the opening 4 of the biogas digester. Preferably, three pin lockers 3 are used for locking up the cover 1 within the inner wall of the opening 4 of the biogas digester.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A bracket type biogas storage cover for a biogas digester, comprising:

a cover having an air vent provided at a top end of said cover, and at least two brackets spacedly provided at a lower opening edge of said cover for coupling with an opening of said biogas digester, wherein said brackets are spacedly provided at said opening edge of said cover, wherein each of said brackets comprises a supporting frame having a triangular shape, and a locking sleeve provided at the vertex of said supporting frame for a pin locker passing through said locking sleeve, wherein said supporting frame has a curved base, wherein said locking sleeve is pivotally coupled at the vertex of said supporting frame, wherein two hypotenuse edge frames of said supporting frame are pivotally coupled with said curved base thereof, wherein said locking sleeve has a horseshoe structure and has two fringes extended from an opening of said locking sleeve, wherein a screw hole is provided at each of said fringes for pivotally connecting to said supporting frame, wherein each of said hypotenuse edge frames has a S-shaped structure and has two screw holes provided at two ends of said hypotenuse edge frame, wherein two connectors are spacedly provided at said curved base, wherein each of said connectors also has a screw hole formed thereon, wherein each of said hypotenuse edge frames is pivotally coupled between said locking sleeve and said curved base by coupling said two ends of said hypotenuse edge frame with said fringe and said respective connector to align said screw holes with each other for screws connecting thereto respectively; and a reinforce ring mounted at said opening edge of said cover, wherein said brackets are mounted at said reinforcing ring, wherein a curvature of said curved base matches with a curvature of a reinforcing ring mounted at said opening edge of said cover.

2. The bracket type biogas storage cover, as recited in claim 1, wherein said cover has a vent hole provided on said cover and comprises a sealing cap sealed and mounted at said vent hole.

3. The bracket type biogas storage cover, as recited in claim 2, wherein said vent hole is provided at said sealing cap.

4. The bracket type biogas storage cover, as recited in claim 1, further comprising a sealing ring sealed at a connection between said sealing cap and said vent hole.

5. The bracket type biogas storage cover, as recited in claim 2, further comprising a sealing ring sealed at a connection between said sealing cap and said vent hole.

6. The bracket type biogas storage cover, as recited in claim 3, further comprising a sealing ring sealed at a connection between said sealing cap and said vent hole.

7. The bracket type biogas storage cover, as recited in claim 2, wherein said sealing cap and said vent hole is coupled by thread.

8. The bracket type biogas storage cover, as recited in claim 3, wherein said sealing cap and said vent hole is coupled by thread.

9. The bracket type biogas storage cover, as recited in claim 5, wherein said sealing cap and said vent hole is coupled by thread.

10. The bracket type biogas storage cover, as recited in claim 6, wherein said sealing cap and said vent hole is coupled by thread.

* * * * *